United States Patent
Kato et al.

(10) Patent No.: US 7,154,008 B2
(45) Date of Patent: Dec. 26, 2006

(54) PRODUCTION METHOD OF ALKYLBENZALDEHYDES

(75) Inventors: Kinji Kato, Okayama (JP); Yoshihiro Shiokawa, Chiba (JP); Tsuyoshi Hatakeyama, Okayama (JP); Mitsuharu Kitamura, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 10/963,572

(22) Filed: Oct. 14, 2004

(65) Prior Publication Data

US 2005/0085670 A1   Apr. 21, 2005

(30) Foreign Application Priority Data

Oct. 17, 2003   (JP) .............................. 2003-357971

(51) Int. Cl.
*C07C 45/49*   (2006.01)
(52) U.S. Cl. ...................... 568/428; 568/433
(58) Field of Classification Search ................ 568/428, 568/433
See application file for complete search history.

(56) References Cited

U.S. PATENT DOCUMENTS

| | | | |
|---|---|---|---|
| 2,485,237 A * | 10/1949 | Gresham et al. ............ 260/599 |
| 4,368,336 A | 1/1983 | Fujiyama et al. |
| 4,460,794 A | 7/1984 | Fujiyama et al. |
| 6,562,996 B1 * | 5/2003 | Saleh .......................... 562/405 |
| 6,881,866 B1 * | 4/2005 | Kato et al. .................. 568/428 |

OTHER PUBLICATIONS

Communication and European Search Report dated Dec. 8, 2004 for No. EP 04 10 4905.

* cited by examiner

*Primary Examiner*—Sikarl A. Witherspoon
(74) *Attorney, Agent, or Firm*—Antonelli, Terry, Stout and Kraus, LLP.

(57) ABSTRACT

In the production of an alkylbenzaldehyde by a method comprising a step of preparing a solution of complex of a starting alkylbenzene and a hydrogen fluoride-boron trifluoride catalyst and a step of formylation by bringing the solution of complex into contact with carbon monoxide, an alkylbenzene having at least one primary alkyl group having two or more carbon atoms on its benzene ring is used as the starting alkylbenzene. The preparation of the solution of complex is carried out in the presence of an aliphatic or alicyclic saturated hydrocarbon having 6 to 10 carbon atoms which contains at least one tertiary carbon atom but contains no quaternary carbon atom. By the combined use of the specific alkylbenzene and the aliphatic or alicyclic saturated hydrocarbon, the disproportionation of the alkylbenzene is prevented and the alkylbenzaldehyde is produced at high yields.

8 Claims, No Drawings

PRODUCTION METHOD OF ALKYLBENZALDEHYDES

BACKGROUND OF THE INVENTION

1. Field of the Invention

The present invention relates to the production of alkylbenzaldehydes which are useful as raw materials or intermediates for perfumes, medicines and agricultural chemicals, more particularly, to the production of alkylbenzaldehydes from alkylbenzenes having a primary alkyl group of two or more carbon atoms.

2. Description of the Prior Art

The production process of an alkylbenzaldehyde by the reaction of an alkylbenzene and carbon monoxide in the presence of a catalyst such as hydrogen chloride-aluminum chloride is well know as Gattermann-Koch reaction. In this process, the regeneration of catalyst is very difficult because the reaction product mixture is usually treated with water after the reaction to facilitate the separation of the product and the catalyst. Another drawback of this process is an increased cost of waste disposal because a large amount of waste is produced by hydrolysis.

A modified Gattermann-Koch reaction using hydrogen fluoride and boron trifluoride as the catalyst is disclosed (U.S. Pat. No. 2,485,237 and JP 39-29760 B). Since hydrogen fluoride and boron trifluoride have high vapor pressures, hydrolysis is not needed to separate the product and the catalyst, this making it possible to recycle the catalyst for reuse. Thus, this process is one of industrially advantageous production methods of aromatic aldehydes.

The process of JP 39-29760 B proceeds according to the following reaction schemes when toluene is used as the starting material.

1. Preparation of solution of toluene/hydrogen fluoride-boron trifluoride complex

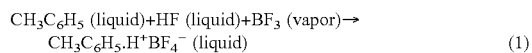

2. Formation of tolualdehyde/hydrogen fluoride-boron trifluoride complex by reaction with carbon monoxide

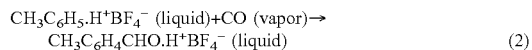

The formylation step (2) requires a higher pressure than required in the step (1) for preparing the solution of complex because the step (2) includes the reaction with carbon monoxide gas. In the proposed process, the supply of a large amount of boron trifluoride gas into a high-pressure reaction system is avoided by preparing the solution of toluene/hydrogen fluoride-boron trifluoride complex in advance.

It has been well known that the hydrogen fluoride-boron trifluoride catalyst is a good catalyst for the formylation on the one hand, but, unfavorably has an extremely high catalytic action for the disproportionation reaction (hereinafter merely referred to "disproportionation") of alkylbenzenes on the other hand (J. Am. Chem. Soc., 75, 2411 (1953).

The disproportionation is particularly remarkable in alkylbenzenes having an alkyl group of two or more carbon atoms. For example, ethylbenzene is disproportionated as follows.

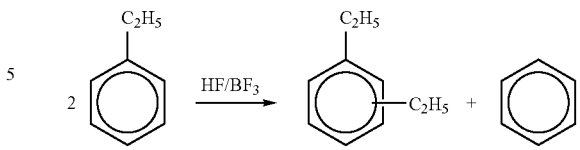

The disproportionation rapidly proceeds even at low temperatures as low as −20° C. and is difficult to prevent. However, an alkylbenzaldehyde resulted from the formylation of an alkylbenzene which is susceptible to disproportionation is stable against disproportionation even in the presence of the hydrogen fluoride-boron trifluoride catalyst. Utilizing this character, a process for producing an alkylbenzaldehyde at high yields has been proposed (JP 62-34024 B), in which the formation of the complex of alkylbenzene and hydrogen fluoride-boron trifluoride and the formylation by carbon monoxide are continuously carried out in a single step to prevent side reactions while introducing an alkylbenzene, hydrogen fluoride-boron trifluoride and carbon monoxide at a partial pressure of 5 kg/cm$^2$ (about 0.5 MPa) or higher into a reactor.

Unlike the process comprising the schemes (1) and (2), however, this process needs the supply of a large amount of boron trifluoride gas into a high-pressure reaction system, because the formation of the alkylbenzene/hydrogen fluoride-boron trifluoride and the formylation by carbon monoxide should be carried out in a single step. Since the reactor is pressurized by carbon monoxide, boron trifluoride should be forced into the reactor after compressed by a gas compressor. Since boron trifluoride is a corrosive gas, the maintenance and inspection of the compressor require much labor.

SUMMARY OF THE INVENTION

An object of the present invention is to provide a method for producing alkylbenzaldehydes at high yields without using a compressor for feeding boron trifluoride even when alkylbenzenes susceptible to disproportionation in the presence of hydrogen fluoride-boron trifluoride catalyst are used as raw materials.

As a result of extensive research in view of achieving the above object, the inventors have found that alkylbenzenes having a primary alkyl group of two or more carbon atoms (the carbon atom of the alkyl group which is bonded to the benzene ring is a secondary carbon atom) are formylated into alkylbenzaldehydes at high yields in the presence of a specific saturated hydrocarbon without causing the disproportionation of the alkylbenzenes even in the presence of a hydrogen fluoride-boron trifluoride catalyst and without using a compressor for feeding boron trifluoride which is required in the process of JP 62-34024 B. The invention has been accomplished on the basis of this finding.

Thus, the invention provides a method of producing an alkylbenzaldehyde comprising a step of preparing a solution of complex of a starting alkylbenzene and a hydrogen fluoride-boron trifluoride catalyst and a step of formylation by bringing the solution of complex into contact with carbon monoxide, wherein the alkylbenzene has at least one primary alkyl group having of two or more carbon atoms on the benzene ring; and wherein the solution of complex was prepared in the presence of an aliphatic or alicyclic saturated hydrocarbon of 6 to 10 carbon atoms which contains at least one tertiary carbon atom but contains no quaternary carbon atom.

In the production method of the invention, the alkylbenzaldehydes are produced at high yields without using a compressor for supplying boron trifluoride even when the alkylbenzenes which are easily disproportionated in the presence of a hydrogen fluoride-boron trifluoride catalyst are used as the starting compounds.

DETAILED DESCRIPTION OF THE INVENTION

The starting alkylbenzene has at least one primary alkyl group of two or more carbon atoms on its benzene ring. The alkyl group should be a primary alkyl group, i.e., the carbon atom in the alkyl group which is directly bonded to the benzene ring should be a secondary carbon atom. The primary alkyl group is represented by the formula:

wherein R is a straight-chain, branched-chain or cyclic saturated hydrocarbon group having 1 to 10 carbon atoms. The alkylbenzenes preferably have one to three primary alkyl groups, and may have one or more methyl groups in addition to the primary alkyl group(s). However, the use of alkylbenzenes having a secondary or tertiary alkyl group such as isopropyl group, sec-butyl group and tert-butyl group should be avoided. In the production method of the invention, alkylbenzenes having no secondary or tertiary alkyl group is used as the starting compounds.

Examples of the alkylbenzenes usable in the invention include monoalkylbenzenes such as ethylbenzene, n-propylbenzene, n-butylbenzene and isobutylbenzene; dialkylbenzenes such as o-, m- or p-ethyltoluene and o-, m- or p-diethylbenzene; and trialkylbenzenes such as 1,2,3-, 1,2,4- or 1,3,5-triethylbenzene.

Hydrogen fluoride is used in an amount of 5 mol or more, preferably 7 mol or more per one mole of the starting alkylbenzene. An amount exceeding 15 mol is not needed because no additional effect is obtained. The amount of boron trifluoride to be used is one mole or more, preferably 1.1 to 2.0 mol per one mole of the starting alkylbenzene.

The temperature of a tank for preparing a solution of a complex of the starting alkylbenzene and a hydrogen fluoride-boron trifluoride catalyst (hereinafter merely referred to as "preparation tank") is preferably controlled so as to maintain the inner pressure of the preparation tank higher than the vapor pressure of the complex and lower than the decomposition pressure of an alkylbenzaldehyde/hydrogen fluoride-boron trifluoride complex being produced. By controlling the temperature and pressure as described above, it becomes possible to recycle and reuse boron trifluoride used as the catalyst without using a compressor for feeding boron trifluoride. The temperature and pressure of the preparation tank are preferably selected from the ranges of −50 to 0° C. and 0.1 to 0.6 MPa so as to meet the requirements mentioned above.

For example, when the decomposition of a complex comprising p-ethylbenzaldehyde derive from ethylbenzene and a hydrogen fluoride-boron trifluoride catalyst is conducted under a pressure of 0.4 MPa, the operation pressure of the preparation tank can be made into 0.35 MPa, a pressure lower than the decomposition pressure, by controlling the temperature of the preparation tank to −20° C., if the molar ratio of ethylbenzene, hydrogen fluoride and boron trifluoride is 1.0:10.0:1.3.

The step for preparing the solution of a complex of the starting alkylbenzene and the hydrogen fluoride-boron trifluoride catalyst by the contact of the starting alkylbenzene and the catalyst should be carried out in the presence of an aliphatic or alicyclic saturated hydrocarbon having 6 to 10 carbon atoms which has at least one tertiary carbon atom but no quaternary carbon atom (hereinafter referred to as "disproportionation inhibitor"). By the addition of such a disproportionation inhibitor, the side reactions such as disproportionation are prevented and the aimed alkylbenzaldehydes are obtained at high selectivity and high yield. The disproportionation inhibitor may be mixed with the starting alkylbenzene in advance in a storage tank of starting materials, or may be mixed in the preparation tank by separately introducing the starting alkylbenzene and the disproportionation inhibitor.

For the disproportionation inhibitor, it is essential to have at least one, usually one or two tertiary carbon atoms, but have no quaternary carbon atom. The disproportionation inhibitor may contain a saturated hydrocarbon such as isooctane having a quaternary carbon atom in an amount not adversely affect the effect of the invention, but generally, it is rather preferred not to contain such a saturated hydrocarbon. Examples of the disproportionation inhibitor include aliphatic hydrocarbons such as isohexane, 3-methylpentane, 2-methylhexane and 2-ethylhexane; and alicyclic hydrocarbons such as decaline, tetrahydrodicyclopentadiene, ethylcyclohexane, methylcyclohexane, dimethylcyclohexane, methylcyclopentane and dimethyicyclopentane, with methylcyclohexane and methylcyclopentane being preferred, and methylcyclopentane being more preferred. The aliphatic hydrocarbon may contain two or more branches.

These disproportionation inhibitors may be used alone or in combination of two or more. Another saturated hydrocarbon having no quaternary carbon atom may be used in an amount not excessively lowers the volume efficiency of the preparation tank. It is undesirable for the invention that the disproportionation inhibitor and other saturated hydrocarbons to be optionally used contain impurities having unsaturated bond or impurities having atoms other than carbon and hydrogen.

The amount of the disproportionation inhibitor to be used is preferably 0.1 to 5.0 mol %, more preferably 0.1 to 2.0 mol %, and still more preferably 0.1 to 1.0 mol % based on the starting alkylbenzene. If less than 0.1 mol %, the effect of preventing side reactions is insufficient. An amount exceeding 5.0 mol % is not preferred, because no additional effect is obtained, and the increase in production costs and the lowering of the volume efficiency of the preparation tank are rather caused.

In the step for preparing the solution of complex, the residence time in the preparation tank is regulated preferably within 0.5 to 5 h by controlling the feeding rate of the raw materials and the discharging rate of the solution of complex (feeding rate into the formylation step).

The solution of complex of the starting alkylbenzene and hydrogen fluoride-boron trifluoride thus prepared is then brought into contact with pressurized carbon monoxide to be immediately converted into a solution of complex of alkylbenzaldehyde/hydrogen fluoride-boron trifluoride by formylation.

The partial pressure of carbon monoxide in the formylation is preferably 0.5 MPa or more, more preferably 1 MPa or more in view of the yield. A partial pressure exceeding 3 MPa is not economically advantageous because no additional effect is obtained. The formylation temperature depends on the kind of the starting alkylbenzene, and is generally lower than room temperature in view of preventing side reactions, preferably −40 to 10° C. The residence time in the formylation reactor is preferably regulated within 0.5 to 10 h by controlling the feeding rate of the solution of complex from the preparation tank and the discharging rate of the formylation product solution.

The solution of complex of the alkylbenzaldehyde and the hydrogen fluoride-boron trifluoride is generally thermally decomposed into a mixture containing the alkylbenzaldehyde and the catalyst component (hydrogen fluoride and boron trifluoride). The thermal decomposition may be conducted by a known method, for example, by a method described in JP 53-14059 B and JP 53-3376 B. More specifically, the thermal decomposition is preferably carried out in the presence of at least one diluent such as benzene, nucleus-fluorinated benzenes and nucleus-fluorinated methylbenzenes under reflux conditions (generally 110 to 170° C.) under 0.2 to 0.7 MPa. During the thermal decomposition, the catalyst component is vaporized and separated from the mixture containing the alkylbenzaldehyde. The separated catalyst component can be reused in the step for preparing the solution of complex. By purifying the mixture by distillation, etc., the aimed alkylbenzaldehyde is obtained.

The present invention will be explained in more detail by reference to the following example which should not be construed to limit the scope of the present invention.

EXAMPLE 1

One of two 1-L jacketed autoclaves equipped with a stirrer was used as a preparation tank for a solution of complex and the other was used as a formylation reactor.

Into the preparation tank, were continuously introduced ethylbenzene containing 0.5 mol % of methylcyclopenatane, hydrogen fluoride and boron trifluoride at respective flow rates of 1.0 mol/h (based on ethylbenzene), 10.0 mol/h and 1.3 mol/h to prepare a solution of complex of ethylbenzene/hydrogen fluoride-boron trifluoride. The solution of complex was continuously pumped into the formylation reactor which had been pressurized by carbon monoxide to a total pressure of 2.0 MPa while maintaining the liquid level so as to control the average residence time in the preparation tank to one hour. The temperature of the preparation tank was controlled to −20° C. by passing a coolant through the jacket, and the pressure was controlled to 0.35 MPa. The temperature of the formylation reactor was maintained at −20° C. by passing a coolant through the jacket. The formylation product solution was continuously discharged while maintaining the liquid level so as to control the average residence time to 1.5 h. During the formylation, carbon monoxide was continuously supplied using a pressure controller so as to maintain the total pressure constant at 2 MPa. The discharged formylation product solution was poured into ice water. After separating the aqueous phase, the oily phase was neutralized and washed with water to obtain an oily substance.

The oily substance was analyzed by gas chromatography. The conversion of ethylbenzene was 90.0 mol % and the selectivity to p-ethylbenzaldehyde was 97.5 mol %. The contents of other alkylbenzaldehydes were 1.0 mol % for o-ethylbenzaldehyde, 0.2 mol % for m-ethylbenzaldehyde and 0.5 mol % for 2,4-diethylbenzaldehyde, each in terms of the selectivity.

EXAMPLE 2

The procedure of Example 1 was repeated except for changing the mixing amount of methylcylcopentane with ethylbenzene to 0.1 mol %. The oily substance obtained by separating the catalyst component from the discharged formylation product solution was analyzed by gas chromatography. The conversion of ethylbenzene was 90.5 mol % and the selectivity to p-ethylbenzaldehyde was 95.5 mol %. The contents of other alkylbenzaldehydes were 1.1 mol % for o-ethylbenzaldehyde, 0.1 mol % for m-ethylbenzaldehyde and 1.5 mol % for 2,4-diethylbenzaldehyde, each in terms of the selectivity.

Comparative Example 1

The procedure of Example 1 was repeated except for introducing a pure ethylbenzene without mixed with methylcyclopentane into the preparation tank. The oily substance obtained by separating the catalyst component from the discharged formylation product solution was analyzed by gas chromatography. The conversion of ethylbenzene was 93.0 mol %, but the selectivity to p-ethylbenzaldehyde was as low as 85.0 mol %. The contents of other alkylbenzaldehydes were 0.9 mol % for o-ethylbenzaldehyde, 0.1 mol % for m-ethylbenzaldehyde and 5.5 mol % for 2,4-diethylbenzaldehyde, each in terms of the selectivity.

EXAMPLE 3

The procedure of Example 1 was repeated except for mixing ethylbenzene with isohexane in place of methylcyclopentane. The oily substance obtained by separating the catalyst component from the discharged formylation product solution was analyzed by gas chromatography. The conversion of ethylbenzene was 90.2 mol % and the selectivity to p-ethylbenzaldehyde was 96.8 mol %. The contents of other alkylbenzaldehydes were 1.0 mol % for o-ethylbenzaldehyde, 0.2 mol % for m-ethylbenzaldehyde and 0.8 mol % for 2,4-diethylbenzaldehyde, each in terms of the selectivity.

EXAMPLE 4

Similarly to Example 1, two 1-L jacketed autoclaves equipped with a stirrer were used, one for a preparation tank for a solution of complex and the other for a formylation reactor.

Into the preparation tank, were continuously introduced isobutylbenzene containing 0.4 mol % of methylcyclopenatane, hydrogen fluoride and boron trifluoride at respective flow rates of 0.9 mol/h (based on isobutylbenzene), 9.0 mol/h and 1.4 mol/h to prepare a solution of complex of isobutylbenzene/hydrogen fluoride-boron trifluoride. The solution of complex was continuously pumped into the formylation reactor which had been pressurized by carbon monoxide to a total pressure of 2.0 MPa while maintaining the liquid level so as to control the average residence time in the preparation tank to one hour. The temperature of the preparation tank was controlled to −25° C. by passing a coolant through the jacket, and the pressure was controlled to 0.37 MPa. The temperature of the formylation reactor was maintained at −15° C. by passing a coolant through the jacket. The formylation product solution was continuously discharged while maintaining the liquid level so as to control the average residence time to 1.5 h. During the formylation, carbon monoxide was continuously supplied using a pressure controller so as to maintain the total pressure constant at 2 MPa. The discharged formylation product solution was poured into ice water. After separating the aqueous phase, the oily phase was neutralized and washed with water to obtain an oily substance.

The oily substance was analyzed by gas chromatography. The conversion of isobutylbenzene was 97.5 mol % and the selectivity to p-isobutylbenzaldehyde was 98.2 mol %. In addition, 2,4-diisobutylbenzaldehyde was contained at a selectivity of 0.1 mol % as another alkylbenzaldehyde.

Comparative Example 2

The procedure of Example 4 was repeated except for introducing a pure isobutylbenzene without mixed with methylcyclopentane into the preparation tank. The oily substance obtained by separating the catalyst component from the discharged formylation product solution was analyzed by gas chromatography. The conversion of isobutylbenzene was 98.0 mol %, but the selectivity to p-isobutylbenzaldehyde was as low as 90.5 mol %. In addition, 2,4-diisobutylbenzaldehyde was contained at a selectivity of 3.8 mol % as another alkylbenzaldehyde.

The alkylbenzaldehydes produced by the method of the invention are useful as the raw materials or intermediates for perfumes, medicines and agricultural chemicals.

What is claimed is:

1. A method of producing an alkylbenzaldehyde from a starting alkylbenzene (A), comprising:
   (I) a step of preparing a solution of complex of said starting alkylbenzene (A) and a hydrogen fluoride-boron trifluoride catalyst (B);
   (II) a step of formylation by bringing the solution of complex into contact with carbon monoxide; and
   (III) a step of decomposition of the produced alkylbenzaldehyde/hydrogen fluoride-boron trifluoride complex to the products of alkylbenzaldehyde and hydrogen fluoride-boron trifluoride catalyst (B),
   wherein:
   (i) the starting alkylbenzene (A) has at least one primary alkyl group having at least two carbon atoms on the benzene ring;
   (ii) the solution of complex was prepared in the presence of a disproportionation inhibitor (C) comprising aliphatic or alicyclic saturated hydrocarbon having 6 to 10 carbon atoms which contains at least one tertiary carbon atom but contains no quaternary carbon atom;
   (iii) the hydrogen fluoride-boron trifluoride catalyst (B) comprises an amount of hydrogen fluoride of 5 mole or more and an amount of boron trifluoride of 1.1 to 2.0 mol per one mole of the starting alkylbenzene (A);
   (iv) the amount of the disproportionation inhibitor (C) is 0.1 to 2.0 mol % based on the starting alkylbenzene (A); and
   (v) the temperature of a tank for preparing a solution of the complex of the starting alkylbenzene (A) and the hydrogen fluoride-boron trifluoride catalyst (B) in step (I) is controlled so as to maintain an inner pressure of the preparation tank higher than a vapor pressure of the complex in step (II) and lower than a decomposition pressure in step (III) of the produced alkylbenzaldehyde/hydrogen fluoride-boron trifluoride complex.

2. The method according to claim 1, wherein the primary alkyl group is represented by the following formula:

wherein R is a straight-chain, branched-chain or cyclic saturated hydrocarbon group having 1 to 10 carbon atoms.

3. The method according to claim 1, wherein the starting alkylbenzene is at least one compound selected from the group consisting of ethylbenzene, n-propylbenzene, n-butylbenzene, isobutylbenzene, o-, m- or p-ethyltoluene, o-, m- or p-diethylbenzene and 1,2,3-, 1,2,4- or 1,3,5-triethylbenzene.

4. The method according to claim 1, wherein the aliphatic or alicyclic saturated hydrocarbon is at least one compound selected from the group consisting of isohexane, 3-methylpentane, 2-methylhexane, 2-ethylhexane, decaline, tetrahydrodicyclopentadiene, ethylcyclohexane, methylcyclohexane, dimethylcyclohexane, methylcyclopentane and dimethylcyclopentane.

5. The method according to claim 1, wherein the starting alkylbenzene (A) has 1–3 primary alkyl groups.

6. The method according to claim 1, wherein the starting alkylbenzene (A) has no secondary or tertiary alkyl groups.

7. The method according to claim 1, wherein the amount of the disproportionation inhibitor (C) is 0.1 to 1.0 mol % based on the starting alkylbenzene (A).

8. The method according to claim 1, wherein temperature and pressure of said preparation tank respectively are in the range of −50 to 0° C. and 0.1 to 0.6 MPa.

* * * * *